United States Patent [19]

Lecloux et al.

[11] 4,384,986
[45] May 24, 1983

[54] PARTICLES OF AN ALLOY OF NOBLE METALS WITH NON-NOBLE METALS

[75] Inventors: Andre Lecloux; Yves Gobillon, both of Brussels, Belgium

[73] Assignee: Solvay & Cie., Brussels, Belgium

[21] Appl. No.: 842,333

[22] Filed: Oct. 14, 1977

[30] Foreign Application Priority Data

Oct. 29, 1976 [LU] Luxembourg .............................. 76107

[51] Int. Cl.³ ........................ B01J 23/46; B01J 23/50; B01J 23/60; B01J 23/64

[52] U.S. Cl. ..................................... 252/456; 252/457; 252/458; 252/460; 252/464; 252/465; 252/466 B; 252/466 PT; 252/469; 252/470; 252/472; 252/473; 252/474; 208/138; 585/419

[58] Field of Search ............... 252/470, 472, 473, 474, 252/439, 460, 466 B, 466 PT, 456, 457, 458, 464, 465, 469; 75/0.5 B, 83, 172 R, 255; 208/138; 260/673.5

[56] References Cited

U.S. PATENT DOCUMENTS

| | | | |
|---|---|---|---|
| 2,906,700 | 9/1959 | Stine et al. ...................... | 252/472 X |
| 3,562,346 | 2/1971 | Smirnov et al. ................ | 252/472 X |
| 3,617,518 | 11/1971 | Sinfelt et al. .................... | 252/474 X |
| 3,759,823 | 9/1973 | Davies et al. ................... | 252/466 B |
| 3,806,446 | 4/1974 | Hayes ........................... | 252/466 PT |
| 3,956,191 | 5/1976 | Cusumano ........................ | 252/474 |
| 3,962,139 | 6/1976 | Van de Moesdijk et al. ... | 252/472 X |
| 4,048,098 | 9/1977 | Koberstein et al. ............ | 252/472 X |

Primary Examiner—W. J. Shine
Attorney, Agent, or Firm—Spencer & Kaye

[57] ABSTRACT

Particles of alloys of a noble metal chosen from among iridium, osmium, palladium, platinum, rhodium and ruthenium, hereafter represented by M, with at least one non-noble metal chosen among silver, bismuth, cadmium, cobalt, copper, tin, germanium, indium, manganese, mercury, molybdenum, nickel, gold, lead, rhenium, thallium, tellurium, technetium, tungsten, vanadium and zinc, hereafter referred to as Me', and Me', representing at least one non-noble metal, characterized in that they correspond to the general formula

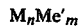

$$M_n Me'_m$$

where n represents an integer equal to 1, 2 or 3 and where m represents an integer equal to 1, 2 or 3, and in that their specific surface area is between 0.5 and 800 m²/g of alloy and in that the mean diameter of the alloy particles is between 10 and 10,000 Å.

The particles are prepared by reducing the mixed oxides of the corresponding formula

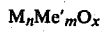

$$M_n Me'_m O_x$$

They are used as catalyst for dehydrogenation or hydrogenation.

18 Claims, No Drawings

PARTICLES OF AN ALLOY OF NOBLE METALS WITH NON-NOBLE METALS

The invention relates to new particles containing an alloy of a noble metal with a non-noble metal. It also relates to a process for their manufacture and to their use as catalysts.

It is difficult to obtain, by the processes of manufacture of alloys by conventional metallurgy, compounds which have a homogeneous and ordered microscopic structure. In general, the alloys obtained contain several phases, or are in the form of non-homogeneous solid solutions on a microscopic scale. Furthermore, these processes do not make it possible to obtain very small particles of dimensions less than 1 micron and of large specific surface area.

Furthermore, when metal compositions consisting of two different metals and having a large specific surface area are prepared by impregnating porous solid supports by means of solutions of salts of the corresponding metals and calcining the impregnated support, the structure of the products obtained is not homogeneous and the two metals are present in very variable ratios which do not correspond to any ratio related to an ordered structure. Furthermore, the products thus obtained contain, within their structure, impurities originating from the anions of the starting salts.

The applicant company has now found new particles of alloys which do not suffer from the above disadvantages of the known products.

The present invention accordingly relates to new particles of alloys of a noble metal chosen from amongst iridium, osmium, palladium, platinum, rhodium and ruthenium, hereafter represented by M, with at least one non-noble metal chosen from amongst silver, bismuth, cadmium, cobalt, copper, tin, germanium, indium, manganese, mercury, molybdenum, nickel, gold, lead, rhenium, thallium, tellurium, technetium, tungsten, vanadium and zinc, hereafter referred to as Me', Me' representing at least one of the said non-noble metals, characterised in that they correspond to the general formula $$M_n Me_m'$$

where n represents an integer equal to 1, 2 or 3 and m represents an integer equal to 1, 2 or 3 and in that their specific surface area is between 0.5 and 800 m²/g of alloy and in that the mean diameter of the alloy particles is between 10 and 10,000 Å.

Preferably, the specific surface area of the alloy particles is between 1 and 500 m²/g of alloy and the mean diameter of the alloy particles is between 20 and 5,000 Å.

The present invention relates more particularly to the particles of alloys of a noble metal such as palladium, iridium, rhodium or ruthenium with silver, bismuth, cadmium, cobalt, copper, molybdenum, tungsten or zinc.

The present invention in particular relates to the particles of alloys of the formula PdCo, PdCu, PdAg, PdSn, PdBi$_2$, PdW, Ir$_2$W, RuCo$_2$, RhAg, RhBi, Rh$_2$Cd, Rh$_2$Co, Rh$_2$Cu, Rh$_2$W, Rh$_2$Mo, Rh$_2$Zn and Rh$_3$V.

The alloy of rhodium and silver which forms the subject of the present invention corresponds to the formula RhAg. It crystallises in the face-centered cubic system and the unit cell parameter is the following:
$a_0 = 4.00$ Å.

The alloy of rhodium and bismuth which forms the subject of the present invention corresponds to the formula RhBi. Its crystallises in the hexagonal system and the unit cell parameters are the following:

$a_0 = 4.08$ Å and $c_0 = 5.56$ Å.

The alloy of rhodium with cadmium which forms the subject of the present invention corresponds to the formula Rh$_2$Cd. It crystallises in the centered cubic system and the unit cell parameter is the following:

$a_0 = 3.18$ Å.

The alloy of rhodium with cobalt which forms the subject of the present invention corresponds to the formula Rh$_2$Co. It crystallises in the face-centered cubic system and the unit cell parameter is the following:

$a_0 = 3.73$ Å.

The alloy of rhodium with copper which forms the subject of the present invention corresponds to the formula Rh$_2$Cu. It crystallises in the face-centered cubic system and the unit cell parameter is the following:

$a_0 = 3.76$ Å.

The alloy of rhodium with molybdenum which forms the subject of the present invention corresponds to the formula Rh$_2$Mo. It crystallises in the hexagonal system and the unit cell parameters are the following:

$a_0 = 2.724$ Å and $c_0 = 4.357$ Å.

The alloy of rhodium with tungsten which forms the subject of the present invention corresponds to the formula Rh$_2$W. It crystallises in the hexagonal system and the unit cell parameters are the following:

$a_0 = 2.730$ Å and $c_0 = 4.40$ Å.

The alloy of rhodium with zinc which forms the subject of the present invention corresponds to the formula Rh$_2$Zn. It crystallises in the centered cubic system and the unit cell parameter is the following:

$a_0 = 2.99$ Å.

The alloy of ruthenium with cobalt which forms the subject of the present invention corresponds to the formula RuCo$_2$. It crystallises in the hexagonal system and the unit cell parameters are the following:

$a_0 = 2.60$ Å and $c_o = 4.16 \text{ Å}$.

In the particles of alloy according to the invention, a non-noble metal can optionally be partially replaced by another non-noble metal of the same valency chosen from amongst those according to the invention. An example of an alloy of this type corresponds to the formula RuCoZn. It crystallises in the hexagonal system and the unit cell parameters are the following:

$a_o = 2.61 \text{ Å}$ and $c_o = 4.18 \text{ Å}$.

The present invention also relates to a process for the manufacture of the alloy particles according to the invention.

The process consists of reducing the mixed oxides of the corresponding metals, which conform to the general formula $M_n Me_m' O_x$ where x is an integer given by the equation $$\frac{(v \cdot n) + (v' \cdot m)}{2}$$

in which v represents the valency of the noble metal M and v' the valency of the non-noble metal Me'.

The mixed oxides $M_n Me_m' O_x$ are in general reduced by passing a stream of gas containing a reducing agent, such as hydrogen, over the said heated mixed oxides. The reaction temperature is between 100° and 650° C. and preferably between 150° and 600° C. The lower temperatures give particularly slow reaction rates which render the process less interesting from an economic point of view. The higher temperatures result in the formation of alloy particles having rather large dimensions. The particles of small dimensions are obtained at the lowest temperatures.

The hydrogen is used by itself or mixed with a gas which is inert towards the mixed oxides under the reduction conditions. The rare gases are very suitable for use as inert gases. Other reducing agents can also be used, such as nitrous oxide and carbon monoxide. The reaction can be carried out in any apparatus which is in itself known. It can be carried out in a fixed bed, or in a fluidised bed, continuously or discontinuously.

The mixed oxides $M_n Me_m' O_x$ used for the manufacture of the alloy particles according to the invention can be obtained by any method which is in itself known. A particularly valuable process consists of reacting at a high temperature, if appropriate under an oxidising atmosphere, an intimate solid mixture of a compound of the noble metal and a compound of the non-noble metal.

The compounds of the noble metal and the compounds of the non-noble metal are chosen from amongst various types of compounds such as the oxides, hydroxides, carbonates, nitrates, formates, acetates, alcoholates, oxalates and chlorides. They can be of the same type or of different types. The oxides of noble metals give good results. As regards the non-noble metals, their oxides, carbonates, nitrates, acetates and chlorides are very suitable. Other compounds of these metals can also be used.

The oxidation temperature is in general between 250° and 1,300° C. and the reaction time varies between 1 hour and 20 days. Other temperatures and other residence times can also be used.

Particular processes for the preparation of the double oxides $Rh_2MoO_6$ and $Rh_2WO_6$ have been described respectively in Luxembourg Patents 61,435 and 62,411, filed on July 29, 1970 and Jan. 13, 1971 in the name of the applicant company.

The alloy particles according to the invention can be obtained as such or can be deposited on a support. They can thus advantageously be deposited on porous supports having a large specific surface area.

Thus, the alloy particles according to the invention can advantageously be deposited on supports such as titanium oxide, various types of alumina and of silica, alumino-silicates and silicates such as zeolites. The best results are obtained when the alloy particles according to the invention are deposited on supports consisting of oxides having crystallographic characteristics compatible with those of the mixed oxide of a noble metal and a non-noble metal which has been used for the manufacture of the alloy particles according to the invention. In general, a support containing an oxide of at least one metal chosen from amongst silicon, aluminium and titanium is used. Titanium oxide has proved particularly advantageous.

A particularly valuable process for the preparation of alloy particles according to the invention deposited on a porous support consists of preparing mixed oxides on the surface of the support and reducing the said supported mixed oxides as indicated above.

The present invention also relates to the use of the alloy particles according to the invention as catalysts. The alloy particles according to the invention are very suitable for use as, in particular, dehydrogenation catalysts or hydrogenation catalysts. Excellent results were obtained when using the alloy particles according to the invention as dehydrogenation catalysts and more particularly as reforming catalysts.

The alloy particles according to the invention are advantageously deposited on a support when they are used as catalysts.

The alloy particles according to the invention are particularly suitable for use as reforming catalysts for the dehydrogenation of saturated hydrocarbons containing from 5 to 20 carbon atoms.

The dehydrogenation reaction is in general carried out at pressures of between 0.8 and 50 kg/cm² and preferably between 0.9 and 20 kg/cm². The dehydrogenation temperature is in general between 150° and 600° C. and preferably between 200° and 500° C. The contact times are usually between 1 second and 1 hour. Other pressures, temperatures and contact times can also be used.

The dehydrogenation reaction can take place in the presence of hydrogen so as to avoid the deactivation of the catalyst. Amounts of between 0.1 and 20 mols of hydrogen per mol of hydrocarbon can be used for this purpose. Other amounts can also be used.

It is also possible to add to the dehydrogenation medium various other additives which are in themselves known for promoting the reaction.

The dehydrogenation process employing the alloy particles according to the invention can be carried out in a fixed bed or in a fluidised bed, continuously or discontinuously.

The use of the alloy particles according to the invention favours the dehydrocyclisation and isomerisation reactions compared to the results obtained with noble metals used separately.

The examples which follow serve to provide a better understanding of the invention and to show the remarkable results obtained when using the alloy particles according to the invention as catalysts, without however limiting the scope of the invention to the embodiments described.

Examples 1 to 10 and 14, 15 show different methods of preparation of the alloy particles according to the invention. Examples 11 and 12 show a process for depositing the alloy particles according to the invention on a porous support. Examples 13 and 16 show the remarkable results obtained when using the alloy particles according to the invention as reforming catalysts.

EXAMPLE 1

$Rh_2Mo$ alloy

The mixed oxide $Rh_2MoO_6$ prepared according to the process described in Luxembourg Patent 61,435 was heated to 500° C. under hydrogen. Differential thermal analysis under hydrogen shows a peak corresponding to the reduction of $Rh_2MoO_6$, the maximum of which is located at 168° C.

The X-ray crystallography analyses carried out on the powder thus obtained showed that the alloy $Rh_2Mo$ crystallises in the hexagonal system, of which the unit cell parameters are the following:

$$a_o = 2.724 \text{ Å}$$

and $$c_o = 4.357 \text{ Å}.$$

The dimensions of the particles are about 20 to 200 Å.

EXAMPLE 2

$Rh_2W$ alloy

The mixed oxide $Rh_2WO_6$ prepared according to the process described in Luxembourg Patent 61,411 was heated to 500° C. under hydrogen. Differential thermal analysis under hydrogen shows a peak corresponding to the reduction of the $Rh_2WO_6$, the maximum of which is located at 205° C.

The X-ray crystallography analyses carried out on the powder thus obtained showed that the alloy $Rh_2W$ crystallises in the hexagonal system, of which the unit cell parameters are the following:

$$a_o = 2.730 \text{ Å}$$

and $$c_o = 4.40 \text{ Å}.$$

The dimensions of the particles are between 20 and 200 Å and their specific surface area is about 30 m²/g.

EXAMPLE 3

$Rh_2Zn$ alloy 1.213 g of ZnO were mixed with 3.786 g of $Rh_2O_3$ to prepare the mixed oxide $Rh_2ZnO_4$. The well-homogenised mixture was subjected to a heat treatment in air for 16 hours at 850° C. The oxide obtained, checked by X-ray diffraction, was reduced by means of a stream of hydrogen and helium (25/75% by volume), the flow rate of which is 50 cm³/minute for 4 hours at 600° C.

The X-ray crystallography analyses carried out on the powder thus obtained showed an alloy $Rh_2Zn$ which crystallises in the centered cubic system, having a structure of the CsCl type, with the unit cell parameter being $a_o = 2.99$ Å.

The dimensions of the particles are between 20 and 200 Å.

EXAMPLE 4

$Rh_2Cd$ alloy 1.395 g of Cd acetate were mixed with 1.328 g of $Rh_2O_3$ to prepare the mixed oxide $Rh_2CdO_4$. The mixture was then ground in an agate mortar so as to give a very homogeneous mixture, which was subjected to a heat treatment for 10 minutes in air at a temperature of 1,000° C. and, after having again ground the product, to a heat treatment of 24 hours at 1,100° C. The mixed oxide $Rh_2CdO_4$ was obtained. The mixed oxide thus obtained was then ground until a particle size equal to less than one micron was obtained, and was then reduced in a stream of hydrogen and helium (25/75% by volume) at a flow rate of 50 cm³/minute, for 4 hours at 300° C.

The X-ray crystallography analyses carried out on the powder thus obtained showed a metallic phase $Rh_2Cd$ which crystallises in the centered cubic system, having a structure of the CsCl type, with the unit cell parameter being $a_o = 3.18$ Å.

The dimensions of the particles are between 20 and 200 Å.

EXAMPLE 5

$Rh_2Co$ alloy 1.140 g of CoO were mixed homogeneously with 3.860 g of $Rh_2O_3$ to prepare $Rh_2CoO_4$. The mixture was subjected to a heat treatment in air for 24 hours at 1,100° C. The X-ray crystallography analyses carried out on the powder thus obtained showed that the mixed oxide crystallises well in the cubic system of the spinel type. Finally, this mixed oxide, $Rh_2CoO_4$, was reduced in a stream of hydrogen and helium (25/75% by volume) at a flow of 50 cm³/minute for 4 hours at 600° C.

The X-ray crystallography analysis of the product obtained showed that the alloy $Rh_2Co$ crystallises in the face-centered cubic system, of which the unit cell parameter is $a_o = 3.73$ Å.

The dimensions of the particles are between 20 and 200 Å.

EXAMPLE 6

RhAg alloy 1.30 g of $Li_2CO_3$ were mixed homogeneously with 4.47 g of $Rh_2O_3$ by means of a ball mill, to prepare $LiRhO_2$. The mixture was subjected to a heat treatment in air for 18 hours at 800° C. The powder obtained was confirmed by X-ray diffraction to be $LiRhO_2$.

4.05 g of $AgNO_3$ and 2.5 g of $KNO_3$ were mixed homogeneously with 1.26 g of $LiRhO_2$. The K nitrate is used as a flux. The mixture thus obtained is placed in a pyrex tube sealed under vacuum and is heat-treated for 5 days at 350° C. The product obtained is washed copiously with demineralised water to remove the Li and K nitrates. The mixed oxide $RhAgO_2$ obtained, checked by X-ray diffraction, was then reduced under a stream of hydrogen and helium (25/75% by volume) at a flow rate of 50 cm$^3$/minute for 4 hours at 300° C.

The X-ray crystallography analyses carried out on the powder thus obtained showed the existence of an alloy RhAg which crystallises in the face-centered cubic system, with the crystalline parameter $a_o=4.00$ Å.

The dimensions of the particles are between 20 and 200 Å.

EXAMPLE 7

RhBi alloy 20.216 g of Bi(NO$_3$)$_3$.5H$_2$O were mixed with 5.289 g of Rh$_2$O$_3$ to prepare the mixed oxide BiRhO$_3$. The mixture was then ground in an agate mortar to give a very homogeneous mixture, which was subjected to a heat treatment for 20 hours at 800° C. The mixed oxide BiRhO$_3$, thus obtained, and checked by X-ray diffraction, was reduced in a stream of hydrogen and helium (25/75% by volume) at a flow rate of 50 cm$^3$/minute for 4 hours at 600° C. Differential thermal analysis under hydrogen shows a peak corresponding to the reduction of BiRhO$_3$, the maximum of which is located at 185° C.

The X-ray crystallography analyses carried out on the reduced mixed oxide showed that the alloy formed crystallises in the hexagonal system with the following crystalline parameters:

$$a_o = 4.08 \text{ Å}$$

and $$c_o = 5.56 \text{ Å}.$$

The dimensions of the particles are between 20 and 200 Å.

EXAMPLE 8

Rh$_2$Cu alloy 1.193 g of CuO were mixed homogeneously with 3.80 g of Rh$_2$O$_3$ by means of a ball mill, to prepare the mixed oxide Rh$_2$CuO$_4$. The mixture was pelleted at ordinary temperature under a pressure of 1,000 kg/cm$^2$ and then subjected to a heat treatment for 2 hours at 750° C., followed by 3 hours at 850° C. in air. The mixed oxide, Rh$_2$CuO$_4$, checked by X-ray diffraction, was reduced under a stream of hydrogen at a flow rate of 100 cm$^3$/minute at a temperature up to 500° C. for about 1 hour. Differential thermal analysis shows an exothermic peak of the reduction of the mixed oxide, the maximum of which is at 167° C.

The X-ray crystallography analysis showed the existence of an alloy Rh$_2$Cu crystallising in the face-centered cubic system and having a crystalline parameter $a_o=3.76$ Å.

The dimensions of the particles are between 20 and 200 Å.

EXAMPLE 9

RuCo$_2$ alloy 1.056 g of CoO were mixed homogeneously with 0.943 g of RuO$_2$ to prepare RuCo$_2$O$_4$. The mixture was then subjected to a heat treatment at 950° C. for 60 minutes in a quartz tube sealed under vacuum. The mixed oxide RuCo$_2$O$_4$ thus obtained and checked by X-ray diffraction, was reduced under a stream of hydrogen and helium (50/50% by volume) at a flow rate of 40 cm$^3$/minute for 4 hours at 500° C.

The alloy formed, RuCo$_2$, crystallises in the hexagonal system, with the following crystalline parameters:

$$a_o = 2.60 \text{ Å}$$

and $$c_o = 4.16 \text{ Å}.$$

The dimensions of the particles are between 20 and 200 Å.

EXAMPLE 10

RuCoZn ternary alloy 0.103 g of CoO and 0.112 g of ZnO were mixed homogeneously with 0.180 g of RuO$_2$ to prepare RuCoZnO$_4$. The mixture was then subjected to a heat treatment at 950° C. for 60 hours in a quartz tube sealed under vacuum. The mixed oxide RuCoZnO$_4$ thus obtained and checked by X-ray diffraction, was reduced under a stream of hydrogen and helium (50/50% by volume) at a flow rate of 40 cm$^3$/minute for 3 hours at 600° C.

The alloy formed, RuCoZn, crystallises in the hexagonal system, with the following crystalline parameters:

$$a_o = 2.61 \text{ Å}$$

and $$c_o = 4.18 \text{ Å}.$$

The dimensions of the particles are between 20 and 200 Å.

EXAMPLE 11

Rh$_2$W alloy deposited on a titanium oxide support

A Ti hydroxide was prepared by precipitating an acid solution of 2.94 g of TiCl$_4$ with ammonia until the pH was 6.

After filtration, washing and drying at 100° C., this precipitate was mixed with 4.08 g of RhCl$_3$.xH$_2$O and 1.80 g of WO$_3$. This mixture is homogenised in a ball mill and calcined at a temperature of 350° C. for 2 hours. The mixture is then ground in an agate mortar so as to give a very homogeneous mixture which was mechanically pelleted at ordinary temperature under a pressure of 400 kg/cm$^2$ and then subjected to a heat treatment for 18 at 950° C. The pellet thus obtained was then ground until a particle size equal to or less than one micron was obtained.

The X-ray crystallography analyses carried out on the powder thus obtained showed the existence of solid solution of the simple oxide TiO$_2$ and the mixed oxide Rh$_2$WO$_6$, in the stoichiometric ratio 2/1. The unit parameters of the square cell of the solid solution Rh$_2$WO$_6$.2TiO$_2$, of the rutile type, are:

$$a_o = 4.63 \text{ Å}$$

and $$c_o = 2.98 \text{ Å}.$$

The solid solution thus obtained was then reduced by means of stream of hydrogen and helium (25/75% by volume) at a flow rate of 50 cm$^3$/minute at 500° C. for 1 hour. The X-ray crystallography analyses carried out on the powder obtained showed the presence of both TiO₂ of the rutile type and of the alloy Rh₂W. A microphotograph, at a magnification of 250,000, taken, by transmission, under an electron microscope, shows that the particles, of about 50 Å, are finely divided and distributed on the surface of the TiO₂.

EXAMPLE 12

Rh₂W alloy deposited on a titanium oxide support

The TiO₂ is prepared by precipitating an acid solution of TiCl₄ with ammonia until the pH is 6, followed by filtration, washing, drying at 100° C. on a ROTAVAPOR (speed 100 revolutions per minute) and calcination at 750° C. for 24 hours.

5 g of TiO₂ were impregnated for 1 hour in a ROTAVAPOR with an ammoniacal solution of H₂WO₄ (257 mg of H₂WO₄ in 50 cm³ of 7 N NH₄OH) and were evaporated to dryness. The product obtained was then impregnated for one hour in a ROTAVAPOR with an aqueous solution of RhCl₃.xH₂O (542 mg of RhCl₃.xH₂O in 50 cm³ of demineralised water). After evaporation to dryness, the product was successively subjected to heat treatments of 2 hours at 350° C., 1 hour at 750° C. and finally 16 hours at 950° C.

The Rh₂WO₆ supported on TiO₂ (and containing 0.5 g of Rh₂WO₆/5 g of TiO₂) is then reduced by means of a stream of hydrogen and helium (25/75% by volume) at a flow rate of 50 cm³/minute for 4 hours at 400° C.

A microphotograph at a magnification of 250,000, taken, by transmission, under an electron microscope, shows particles of Rh₂W of about 50 Å distributed over the TiO₂ support.

EXAMPLE 13

"Reforming" test

A stream of gas containing hydrogen and helium in the ratio of 79-21% by volume is bubbled through liquid heptane heated to 40° C. so as to give a volume ratio of hydrogen:heptane equal to 4.7 in the new gas phase thus obtained. This new gas phase passes over a catalyst such as that described in Example 2, arranged in a fixed bed on a sintered glass plate heated to a temperature of 417° C.

Chromatographic analysis of the reaction products shows the presence of significant amounts of isomerisation and dehydrocyclisation products such as toluene, benzene, cyclohexane, 1,3-dimethylcyclopentane, cyclopentane, methylcyclohexane, methylcyclopentane, methylpentane, 2- and 3-methylhexane, 1-hexane, 4- and 2-methyl-1-pentene and hexane.

The results obtained show the remarkable efficiency of the alloy particles according to the invention as a reforming catalyst.

EXAMPLE 14

PdCo alloy 0.422 g of CoO were mixed with 0.500 g of PdCl₂ to prepare PdCoO₂. The mixture was then ground in an agate mortar so as to give a very homogeneous mixture, which was subjected to a heat treatment for 10 minutes in air at a temperature of 700° C. and, after having again ground the product, to a heat treatment of 16 hours at 700° C. The mixed oxide PdCoO₂ was obtained. The product obtained is washed copiously with demineralised water to remove CoCl₂, treated with bromine water for 30 minutes, washed again and treated with aqua regia for 30 minutes.

After filtration and washing with water, the mixed oxide PdCoO₂ obtained, checked by X-ray diffraction, was then reduced under a stream of hydrogen and helium (25/75% by volume) at a flow rate of 50 cm³/minute for 3 hours at 300° C.

The X-ray crystallography analysis carried out on the powder thus obtained showed the existence of an alloy PdCo which crystallises in the face-centered cubic system with the crystalline parameter $a_o = 3.75$ Å.

The dimensions of the particles are between 20 and 200 Å.

EXAMPLE 15

PdBi₂ alloy 1.583 g of Bi₂O₃ were mixed homogeneously with 0.417 g PdO to prepare PdBi₂O₄. The mixture was then subjected to a heat treatment in air at 700° c. for 60 hours. The oxide obtained, confirmed by X-ray diffraction, was reduced in a stream of hydrogen and helium (25/75% by volume) at a flow of 50 cm³/minute for 2 hours at 620° C.

The X-ray crystallography analysis of the powder obtained showed the existence of an alloy PdBi₂ which crystallises in the monoclinic system with the crystalline parameters $a_o = 12.72$ Å, $b_o = 4.28$ Å, $c_o = 5.66$ Å and $\beta = 102° 50'$.

The dimensions of the particles are between 20 and 200 Å.

EXAMPLE 16

"Reforming" test

The same test as the one described in example 13 was performed with a catalyst such as that described in Example 1. The temperature of the bed was of 402° C.

As in example 13 significant amounts of isomerisation and dehydrocyclisation products were produced. This shows the remarkable efficiency of the alloy particles according to the invention as a reforming catalyst.

We claim:

1. Alloy particles having a homogeneous and ordered microscopic structure, wherein said particles correspond to the general formula:

$$M_n Me'_m$$

wherein M is rhodium and Me' is selected from the group consisting of silver, bismuth, cadmium, cobalt, copper, molybdenum, tungsten, and zinc; m is 1 and n is a whole integer from 1 to 2; said particles have a specific surface area between 0.5 and 800 m²/g of alloy and a mean diameter of between 10 and 10,000 Å, and said alloy particles are prepared by reducing a mixed oxide of the general formula $$M_n Me'_m O_x$$

wherein x is an integer equal to $(3n + v')/2$ and wherein v' is the valence of the metal Me.

2. Alloy particles according to claim 1 wherein the specific surface area of the alloy particles is between 1 and 500 m²/g of alloy and the mean diameter of the alloy particles is between 20 and 5,000 Å.

3. Alloy particles according to claim 1, wherein said particles correspond to the formula RhAg, and crystallise in the face-centered cubic system, the unit cell parameter being $a_o = 4.00$ Å.

4. Alloy particles according to claim 1, wherein said particles correspond to the formula RhBi, and crystallise in the hexagonal system, the unit cell parameters being $a_o = 4.08$ Å and $c_o = 5.56$ Å.

5. Alloy particles according to claim 1, wherein said particles correspond to the formula $Rh_2Cd$, and crystallise in the centered cubic system, the unit cell parameter being $a_o=3.18$ Å.

6. Alloy particles according to claim 1, wherein said particles correspond to the formula $Rh_2Co$, and crystallise in the face-centered cubic system, the unit cell parameter being $a_o=3.73$ Å.

7. Alloy particles according to claim 1, wherein said particles correspond to the formula $Rh_2Cu$, and crystallise in the face-centered cubic system, the unit cell parameter being $a_o=3.76$ Å.

8. Alloy particles according to claim 1, wherein said particles correspond to the formula $Rh_2Mo$, and crystallise in the hexagonal system, the unit cell parameters being $a_o=2.724$ Å and $c_o=4.357$ Å.

9. Alloy particles according to claim 1, wherein said particles correspond to the formula $Rh_2W$, and crystallise in the hexagonal system, the unit cell parameters being $a_o=2.730$ Å and $c_o=4.40$ Å.

10. Alloy particles according to claim 1, wherein said particles correspond to the formula $Rh_2Zn$, and crystallise in the centered cubic system, the unit cell parameter being $a_o=2.99$ Å.

11. Alloy particles according to claim 1, wherein said particles are deposited on a porous inert support.

12. Alloy particles according to claim 11, wherein the porous support contains an oxide of at least one metal selected from the group consisting of silicon, titanium and aluminum.

13. Alloy particles according to claim 1, wherein the reduction takes place in the presence of a stream of gas containing hydrogen.

14. Alloy particles according to claim 1, wherein the reduction takes place at a temperature of between 100° and 650° C.

15. Alloy particles having a homogeneous and ordered microscopic structure, said particles correspond to the formula $RuCo_2$, and crystallize in the hexagonal system, the unit cell parameters being $a_o=2.60$ Å and $c_o=4.16$ Å, and said particles have a specific surface area between 0.5 and 800 m²/g of alloy and a mean diameter of between 10 and 10,000 Å, said alloy particles prepared by reducing a mixed oxide of the formula $RuCo_2O_4$.

16. Alloy particles having a homogeneous and ordered microscopic structure, said particles correspond to the formula $RuCoZn$, and crystallize in the hexagonal system, the unit cell parameters being $a_o=2.61$ Å and $c_o=4.18$ Å, and said particles have a specific surface area between 0.5 and 800 m²/g of alloy and a mean diameter of between 10 and 10,000 Å, said alloy particles prepared by reducing a mixed oxide of the formula $RuCoZnO_4$.

17. Alloy particles having a homogeneous and ordered microscopic structure, said particles correspond to the formula $PdCo$, and crystallize in the face-centered cubic system, the unit cell parameters being $a_o=3.75$ Å and said particles have a specific surface area between 0.5 and 800 m²/g of alloy and a mean diameter of between 10 and 10,000 Å, said alloy particles prepared by reducing a mixed oxide of the formula $PdCoO_2$.

18. Alloy particles having a homogeneous and ordered microscopic structure, said particles correspond to the formula $PdBi_2$, and crystallize in the monoclinic system, the unit cell parameters being $a_o=12.72$ Å and $b_o=4.28$ Å, $c_o=5.66$ Å, and $\beta=102°\ 50'$, and said particles have a specific surface area between 0.5 and 800 m²/g of alloy and a mean diameter of between 10 and 10,000 Å, said alloy particles prepared by reducing a mixed oxide of the formula $PdBi_2O_4$.

* * * * *